(12) United States Patent
Hanks

(10) Patent No.: US 11,858,872 B2
(45) Date of Patent: Jan. 2, 2024

(54) HIGH YIELD JET FUEL FROM MIXED FATTY ACIDS

(71) Applicant: ExxonMobil Research and Engineering Company, Annandale, NJ (US)

(72) Inventor: Patrick L. Hanks, Bridgewater, NJ (US)

(73) Assignee: ExxonMobil Technology and Engineering Company, Annandale, NJ (US)

(*) Notice: Subject to any disclaimer, the term of this patent is extended or adjusted under 35 U.S.C. 154(b) by 0 days.

(21) Appl. No.: 17/216,792

(22) Filed: Mar. 30, 2021

(65) Prior Publication Data

US 2022/0315508 A1 Oct. 6, 2022

(51) Int. Cl.
*C07C 1/207* (2006.01)
*C07C 51/377* (2006.01)
(Continued)

(52) U.S. Cl.
CPC ......... *C07C 1/2078* (2013.01); *B01J 31/2278* (2013.01); *C07C 1/24* (2013.01);
(Continued)

(58) Field of Classification Search
CPC ....... C07C 1/2078; C07C 5/03; C07C 51/377; C07C 1/24; C07C 5/22; C07C 2531/22;
(Continued)

(56) References Cited

U.S. PATENT DOCUMENTS

2005/0070750 A1* 3/2005 Newman .................. C07C 7/04
585/643
2009/0270668 A1* 10/2009 Bailey ....................... C07C 1/24
585/639
(Continued)

FOREIGN PATENT DOCUMENTS

WO  WO 89/03419      * 4/1989
WO  WO-2009038740 A2 * 3/2009 ............ B01J 29/703
(Continued)

OTHER PUBLICATIONS

Wang et al., "Highly efficient conversion of plant oil to bio-aviation fuel and valuable chemicals by combination of enzymatic transesterification, olefin cross-metathesis, and hydrotreating", Biotechnology for Biofuels (2018) 11:30, https://doi.org/10.1186/s13068-018-1020-4.
(Continued)

*Primary Examiner* — Thuan D Dang
(74) *Attorney, Agent, or Firm* — Shook, Hardy & Bacon L.L.P.

(57) ABSTRACT

Disclosed herein are processes and systems that utilize olefin cross metathesis of triglycerides to produce jet fuel such as hydrocarbons with carbons numbers from C9 to C16. Jet range hydrocarbons may include paraffins, naphthenes, and aromatics with carbon numbers from 9 to 16 (C9-C16), and isomers thereof. The process described herein is versatile and may be suitable for producing jet range hydrocarbons from many different grades and sources of triglycerides.
(Continued)

Further, the process described herein may be selective to jet range hydrocarbons which may result in increased yield as compared to hydrocracking or other processes for producing jet range hydrocarbons from triglycerides.

20 Claims, 3 Drawing Sheets

(51) Int. Cl.
  *C10L 1/16* (2006.01)
  *C07C 5/03* (2006.01)
  *C07C 5/22* (2006.01)
  *B01J 31/22* (2006.01)
  *C07C 1/24* (2006.01)

(52) U.S. Cl.
  CPC .................. *C07C 5/03* (2013.01); *C07C 5/22* (2013.01); *C07C 51/377* (2013.01); *C10L 1/1608* (2013.01); *B01J 2231/543* (2013.01); *C07C 2531/22* (2013.01); *C10L 2200/043* (2013.01); *C10L 2200/0469* (2013.01)

(58) Field of Classification Search
  CPC ........... C10L 1/1608; C10L 2200/0469; C10L 2200/043; B01J 31/2278; B01J 2231/543
  See application file for complete search history.

(56) References Cited

U.S. PATENT DOCUMENTS

| | | | |
|---|---|---|---|
| 2011/0160502 A1* | 6/2011 | Wu | C07C 2/30 585/16 |
| 2011/0188202 A1* | 8/2011 | Han | C08L 91/00 361/699 |
| 2012/0197050 A1 | 8/2012 | Joshi et al. | |

FOREIGN PATENT DOCUMENTS

| | | |
|---|---|---|
| WO | 2011/046872 A1 | 4/2011 |
| WO | 2021/028833 A1 | 2/2021 |

OTHER PUBLICATIONS

The International Search Report and Written Opinion for PCT/US2021/024764 dated Nov. 30, 2021.

* cited by examiner

HIGH YIELD JET FUEL FROM MIXED FATTY ACIDS

FIELD OF THE INVENTION

This application relates to processes and systems that utilize olefin cross metathesis of triglycerides to produce jet fuel such as hydrocarbons with carbons numbers from C9 to C16.

BACKGROUND OF THE INVENTION

Aviation is difficult industry to decarbonize due to the need for energy dense fuel sources. Conventional jet fuels are advantageous as they are readily produced from fractional distillation of crude oil, have high energy density, and are liquid across a broad range of temperatures and pressures. The hydrocarbons in jet fuel are typically mixtures of paraffin, naphthene, and aromatics with carbon numbers from 9 to 16 (C9-C16). Jet fuels are typically formulated with various ratios of isomers of the C9-C16 hydrocarbons to provide the desired cold pour properties, freezing point, density, auto-ignition temperature, and other physical properties.

While there has been strong interest in the industry to produce a bio-jet fuel derived partially or entirely from renewable resources, there are few natural sources of fatty acid chains that can be used to produce jet fuel within the acceptable C9-C16 carbon range. Commercially available fats and oils are relatively expensive starting materials and any inefficiencies in the process which reduce yield increase the cost of the final jet fuel product. Coconut oils, for example, have carbon chain lengths from C16 to C18, which can be hydrocracked to produce jet fuels. However, the resultant C8 and C9 hydrocarbons are on the extreme tail end of what is acceptable for use as jet fuel. Further, the hydrocracking process produces significant quantities of light ends paraffinic naphtha, thereby reducing the overall yield of jet fuel.

SUMMARY OF THE INVENTION

Disclosed herein are example processes and systems that utilize olefin cross metathesis of triglycerides to produce jet fuel such as hydrocarbons with carbons numbers from C9 to C16. A methods for producing jet range hydrocarbons may include: hydrolyzing a triglyceride stream in a hydrolysis unit to produce at least a C18:1 free fatty acid, wherein the triglyceride stream comprises at least one triglyceride comprising at least one C18:1 fatty acid, wherein hydrolyzing the triglyceride stream comprises contacting the at least one triglyceride from the triglyceride stream with at least one of water or steam at conditions sufficient to hydrolyze at least a portion of the at least one triglyceride to produce the C18:1 free fatty acid; introducing the C18:1 free fatty acid into an olefin cross-metathesis reactor and reacting at least a portion of the C18:1 free fatty acid with ethylene in the presence of a Grubbs catalyst to produce 1-decene and 9-decanoic acid; introducing the 1-decene and 9-decanoic acid into a hydrotreating unit and hydrotreating at least a portion of the 1-decene and 9-decanoic acid to produce decane; and introducing the decane into an isomerization unit and isomerizing at least a portion of the decane to produce iso-decane.

Further disclosed herein is a method for producing jet range hydrocarbons comprising: counter-currently contacting a triglyceride stream and steam in a column hydrolysis unit to produce at least a C18:1 free fatty acid stream, wherein the triglyceride stream comprises at least one triglyceride comprising at least one C18:1 fatty acid; introducing the C18:1 free fatty acid stream into an olefin cross-metathesis reactor and reacting at least a portion of the C18:1 free fatty acid with ethylene in the presence of a Grubbs catalyst to produce a 1-decene and 9-decanoic acid stream; introducing the 1-decene and 9-decanoic acid stream into a hydrotreating unit and hydrotreating at least a portion of the 1-decene and 9-decanoic acid to produce a decane stream; introducing the decane stream into an isomerization unit and isomerizing at least a portion of the decane stream to produce an iso-decane stream; and separating at least a portion of the iso-decane stream to produce a jet range hydrocarbon stream.

Further disclosed herein is a system for producing jet range hydrocarbons comprising: a triglyceride source comprising at least one C18:1 fatty acid; a hydrolysis unit coupled to the triglyceride source and a steam source, wherein the hydrolysis unit is configured to hydrolyze at least a portion of the triglyceride source to produce a free fatty acid stream comprising free fatty acids corresponding to triglycerides in the triglyceride source, wherein the free fatty acid stream comprises at least C18:1 fatty acid; a separation unit coupled to the free fatty acid stream, wherein the separation unit is configured to separate a majority of the C18:1 fatty acid from the free fatty acid stream to produce a C18:1 fatty acid stream; an olefin cross metathesis reactor coupled to the C18:1 fatty acid stream, wherein the olefin cross metathesis reactor is configured to react the C18:1 fatty acid with ethylene to produce a stream comprising 1-decene and 9-decanoic acid; a hydrotreating unit coupled to the stream comprising 1-decene and 9-decanoic acid, wherein the hydrotreating unit is configured to hydrotreat at least a portion of the 1-decene and 9-decanoic acid to produce a hydrotreated product stream comprising decane; and an isomerization unit coupled to the hydrotreated product stream, wherein the isomerization unit is configured to isomerize at least a portion of the decane to produce an isomerized product stream comprising iso-decane.

BRIEF DESCRIPTION OF THE DRAWINGS

The drawings illustrate certain aspects of the present disclosure and should not be used to limit or define the disclosure.

DETAILED DESCRIPTION OF THE INVENTION

Figure 1:
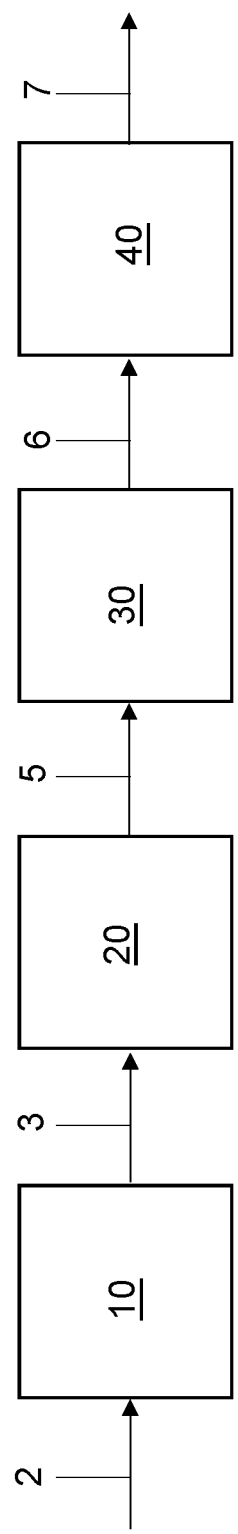
FIG. 1 is a block flow diagram of a process for producing jet range hydrocarbons from triglycerides.

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure.

This application relates to methods and systems for producing jet range hydrocarbons from triglycerides sourced from natural sources. Jet range hydrocarbons may include paraffins, naphthenes, and aromatics with carbon numbers from 9 to 16 (C9-C16), and isomers thereof. The process described herein is versatile and may be suitable for producing jet range hydrocarbons from many different grades and sources of triglycerides. Further, the process described herein may be selective to jet range hydrocarbons which may result in increased yield as compared to hydrocracking or other processes for producing jet range hydrocarbons from triglycerides. The processes described herein may include several unit operations including hydrolysis of the triglycerides to produce fatty acids and olefin cross metathesis of the fatty acids to produce the jet range hydrocarbons. While the processes described herein may be suitable for use for a variety of triglycerides, the process may be particularly suited for triglycerides which produce fatty acids where the carbon chain is 18 carbons long with the double bond on the $9^{th}$ carbon, sometimes referred to as C 18:1.

There are several potential advantages to the methods and systems disclosed herein, only some of which are alluded to in the present disclosure. As discussed above, current techniques for producing jet range hydrocarbons from triglycerides can be problematic due to the relatively high cost of materials and production of products which fall outside the acceptable carbon number range of jet fuel. The olefin cross metathesis described herein provides a scalable process with improved kinetics and selectivity to jet range hydrocarbons without the typical problems associated with low jet range hydrocarbon yield.

Embodiments of the methods and systems described herein may include triglyceride as a starting material. Suitable triglycerides may include any triglyceride which includes at least one unsaturated fatty acid molecule with a carbon chain length of at least C18 to C32 and at least one unsaturated bond on at least the $9^{th}$ carbon or greater. Any symmetrical or unsymmetrical triglyceride which meets these constraints may be used in the present process. While in principle, any triglyceride with any degree of unsaturation may be utilized, each degree of unsaturation of the fatty acid will result in a separate hydrocarbon molecule in the olefin cross metathesis reaction thereby potentially reducing the yield to jet range hydrocarbons as hydrocarbons outside of the C9-C16 range may be produced. As such, at least a portion of the triglyceride should contain at least one fatty acid with a carbon number from C18-C32 and a single degree of saturation on the $9^{th}$ carbon. One example of a suitable triglyceride may include triolein which is a symmetrical triglyceride derived from glycerol and three units of oleic acid.

The triglyceride may be from any source including natural sources such as a seed and/or plant oils. Some example sources may include, without limitation, soy oil, canola oil, camelina oil, olive oil, macadamia oil, sunflower oil, and combinations thereof. Examples of vegetable oils that can be used in accordance with this invention include, but are not limited to rapeseed (canola) oil, soybean oil, sunflower oil, palm oil, palm kernel oil, peanut oil, linseed oil, tall oil, corn oil, castor oil, jatropha oil, jojoba oil, olive oil, flaxseed oil, camelina oil, safflower oil, babassu oil, and rice bran oil. Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans*, *Scenedesmus dimorphus*, *Euglena gracilis*, *Phaeodactylum tricornutum*, *Pleurochrysis camerae*, *Prymnesium parvum*, *Tetraselmis chui*, and *Chlamydomonas reinhardtii*. Additional or alternate algal sources can include one or more microalgae of the *Achnanthes*, Amphiprora, Amphora, Ankistrodesmus, Asteromonas, Boekelovia, Borodinella, Botryococcus, Bracteococcus, Chaetoceros, *Carteria*, *Chlamydomonas*, *Chlorococcum*, Chlorogonium, *Chlorella*, *Chroomonas*, *Chrysosphaera*, *Cricosphaera*, *Crypthecodinium*, Cryptomonas, *Cyclotella*, *Dunaliella*, Ellipsoidon, Emiliania, Eremosphaera, Ernodesmius, *Euglena*, Franceia, *Fragilaria*, Gloeothamnion, *Haematococcus*, Halocafeteria, Hymenomonas, *Isochrysis*, Lepocinclis, Micractinium, Monoraphidium, Nannochloris, *Nannochloropsis*, *Navicula*, *Neochloris*, Nephrochloris, Nephroselmis, *Nitzschia*, Ochromonas, *Oedogonium*, Oocystis, Ostreococcus, *Pavlova*, Parachlorella, Pascheria, *Phaeodactylum*, *Phagus*, Platymonas, *Pleurochrysis*, *Pleurococcus*, *Prototheca*, Pseudochlorella, Pyramimonas, Pyrobotrys, *Scenedesmus*, Skeletonema, Spyrogyra, Stichococcus, *Tetraselmis*, *Thalassiosira*, Viridiella, and *Volvox* species, and/or one or more cyanobacteria of the *Agmenellum, Anabaena, Anabaenopsis*, *Anacystis, Aphanizomenon, Arthrospira*, Asterocapsa, *Borzia, Calothrix, Chamaesiphon, Chlorogloeopsis*, Chroococcidiopsis, *Chroococcus*, Crinalium, Cyanobacterium, Cyanobium, Cyanocystis, *Cyanospira*, Cyanothece, *Cylindrospermopsis, Cylindrospermum*, Dactylococcopsis, Dermocarpella, *Fischerella*, Fremyella, Geitleria, Geitlerinema, Gloeobacter, *Gloeocapsa*, *Gloeothece*, Halospirulina, Iyengariella, *Leptolyngbya*, Limnothrix, *Lyngbya*, *Microcoleus, Microcystis, Myxosarcina, Nodularia, Nostoc*, *Nostochopsis*, *Oscillatoria*, *Phormidium*, *Planktothrix*, *Pleurocapsa, Prochlorococcus*, Prochloron, Prochlorothrix, *Pseudanabaena, Rivularia, Schizothrix, Scytonema, Spirulina*, Stanieria, Starria, *Stigonema, Symploca, Synechococcus, Synechocystis, Tolypothrix, Trichodesmium*, Tychonema, and *Xenococcus* species. Alternatively, or in addition to seed and/or plant oils, the triglyceride may be sourced from an algae that is capable of producing triglycerides which include at least one unsaturated fatty acid molecule with a carbon chain length of at least C18 to C32 and at least one unsaturated bond on at least the $9^{th}$ carbon or greater. The algae strain may be selected for its tendency to produce the triglyceride described above or may be genetically engineered to produce triglycerides with the properties suitable for production of jet range hydrocarbons.

A first step in the process can include converting the triglyceride to the corresponding fatty acids and glycerol by hydrolyzing the triglyceride, sometimes referred to as fat splitting. One suitable method may be the continuous Colgate-Emery process, where nearly complete (>95%) hydrolysis can be achieved by operating around 200-260° C. and pressures up to 50 barg. The reaction may be carried out counter-currently with fat addition at the bottom of the tower and water added at the top of the tower. Residence times of both phases may be on the order of 2-3 hours. The hydrolysis may be performed by contacting the triglyceride with steam at conditions which convert at least a portion of the triglyceride into the corresponding fatty acids and glycerol. The hydrolysis reaction may be carried out in a hydrolysis reactor such as a batch reactor whereby steam may be sparged into the batch reactor until the desired fraction of triglyceride has been converted. Alternatively, hydrolysis may be carried out continuously by counter-currently contacting the triglyceride with steam in a column-type reactor, for example, where the triglyceride is introduced into a top of the column-type reactor and steam is sparged into the bottom of the column-type reactor. The steam may ascend through the column reactor and contact the triglyceride thereby breaking the triglyceride into the corresponding fatty acids and glycerol. Glycerol may be stripped from the fatty acids by the steam and carried out of the column-type reactor as an overhead stream while the fatty acids formed may be drawn off as a bottoms stream.

The steam used in the hydrolysis reaction may be at any temperature and pressure suitable to hydrolyze the triglyceride without substantially polymerizing the resultant fatty acids. For example, the steam may be at a temperature of about 200° C. to about 260° C. and at a pressure of up to about 50 barg. In some examples, the conversion of the triglyceride to fatty acid may be in the range of 10% to 99%, depending on the residence time of the hydrolysis reactor. Hydrolysis may be rate limited by kinetics such that a longer residence time may generally correspond to greater conversion of the triglyceride. In some embodiments, an additional catalyst may be utilized to increase reaction rate. After the hydrolysis step, the fatty acids and glycerol may be separated, for example by stripping the glycerol from the fatty acids using steam or adding water to the glycerol/fatty acid product thereby dissolving at least a portion of the glycerol in an aqueous phase which may then be removed by separating the aqueous phase from a fatty acid phase. Alternatively, the fatty acids and glycerol may be separated by distillation to produce a fatty acid steam with reduced glycerol content.

Lower carbon number unsaturated fatty acids generated during the hydrolysis step may not be suitable for olefin cross metathesis as the resultant hydrocarbons may be outside the suitable carbon numbers for jet fuel. As discussed above, the lowest carbon number typically suitable for jet fuel is C9 and as such, any fatty acids with carbon numbers less than C18 may generate hydrocarbons outside jet fuel range when cross metathesized. Another step may be to fractionate the fatty acids generated in the hydrolysis before cross metathesis such that hydrocarbons generated are within the jet hydrocarbon range. The fatty acids may be fractionated by distillation, for example, to generate a bottoms stream with C18 and heavier fatty acids and an overheads stream with C17 and lighter fatty acids. The C18 and heavier stream may include C18s, such as stearic acid (C18:0), oleic acid (C18:1), and linoleic acid (C18:2), for example. In some embodiments, the C18 and heavier stream may further include heavier saturated fatty acids such as arachidic acid and behenic acid, and heavier unsaturated fatty acids such as arachidonic acid, for example. The C18s may be fractionated further to produce a C18:1 oleic acid stream and a stream containing C18:0 and C18:2, if present. In some examples, additional fractionation aids such as urea and/or methanol may be utilized during fractionation to further separate the fatty acids. Alternatively, or in addition for fractionation, the fatty acids may be further purified by crystallization techniques such as extractive crystallization to separate saturated fatty acids from unsaturated fatty acids.

A second step in the process can involve reacting the C18:1 fatty acid produced from hydrolysis with ethylene in an olefin cross metathesis reactor to produce 1-decene and 9-decenoic acid. The olefin cross metathesis reactor may include a Grubbs catalyst such as a first-generation Grubbs catalyst, second generation Grubbs catalyst, third generation Grubbs catalyst, or combinations thereof. The C18:1 fatty acid and ethylene may be introduced into the reactor and contacted with the Grubbs catalyst, thereby reacting at least a portion of the C18:1 fatty acid to produce the 1-decene and 9-decanoic acid. In some embodiments, the metathesis reactor may be operated at a temperature in a range of 40° C. to about 120° C. Alternatively, the cross metathesis reactor may be operated at a temperature in a range of about 30° C. to about 45° C., about 45° C. to about 50° C., about 50° C. to about 75° C., about 75° C. to about 90° C., or any ranges therebetween. In some embodiments, the cross metathesis reactor may be operated at a pressure of about 10-50 barg partial pressure of ethylene. In some examples, ethylene may be provided in a stoichiometric ratio with C18:1 or may be provided in excess of stoichiometric by about 5% to about 50%. Alternatively, the ethylene may be provided in an amount of about 5% to about 20% excess, about 20% to about 35% excess, or about 35% to about 50% excess. Without being limited by theory, the extent of reaction of the cross-metathesis reaction of ethylene with C18:1 fatty acid may be limited by kinetics. As such, the longer the reaction is allowed to proceed, the greater the extent of reaction may tend to be. Conversion of 90% or greater by weight of the C18:1 fatty acid may be realized by relatively longer reactor residence time. For example, residence times may be between about 1 hour to about 6 hours when utilizing a Grubbs catalyst.

In some embodiments, the ethylene used in the metathesis reaction may be provided by the dehydration of ethanol. For example, ethanol may be dehydrated by concentrated sulfuric acid, concentrated phosphoric acid, or any other suitable acid dehydration agent such as alumina solid catalyst in a fixed bed reactor. One advantage of utilizing ethanol for production of ethylene may be that ethanol may be produced from naturally occurring sources such as crops grown on-purpose for ethanol production. Thus, ethylene derived from natural sources in conjunction with olefin cross metathesis of fatty acids derived from triglycerides ensures that all carbon in the jet grade hydrocarbons is derived from natural sources. Alternatively, the ethylene may be provided from on-purpose ethylene production from steam cracking, oxidative coupling of methane, catalytic dehydrogenation such as by passing ethane over a dehydration catalyst, such as ZSM-5, or any other method to produce ethylene.

While the 1-decene and 9-decanoic acid produced in the cross metathesis reactor may be suitable for inclusion in jet fuel blends, the 1-decene and 9-decanoic acid may be readily upgraded by hydrogenation to improve the properties for blending in jet fuel. Hydrotreating units may utilize hydrotreating catalysts such as sulfides of Co and Mo or Ni and Mo on a support to catalyze the addition of hydrogen to a feed material. Additionally, platinum or palladium without sulfur may be utilized for deoxygenation and olefin saturation. Hydrotreating catalysts may be affected by the presence of oxygen in the 9-decanoic acid thereby reducing the activity of the hydrotreating catalyst. It may be advantageous to utilize a standalone hydrotreating unit, separate from other hydrotreating units in a chemical plant and/or refinery, for upgrading the stream from the cross-metathesis reactor such that the acid does not deactivate the catalyst for the entire plant. In a standalone hydrotreating unit, the 1-decene and 9-decanoic acid can be simultaneously upgraded to straight chain decane paraffin. In addition to 1-decene and 9-decanoic acid, other saturated and unsaturated fatty acids produced in the hydrolysis reactor may be introduced into the hydrotreating unit to be converted to their corresponding paraffins. While the straight chain decane is within the jet range hydrocarbons, decane may not have the physical properties such as cold pour point, freezing point, density, and octane value required for jet fuel. As such, the decane may be further isomerized in an isomerization unit to produce iso-decane with properties that align with the desired properties of jet fuel.

In an embodiment, the 1-decene and 9-decanoic acid produced in the cross metathesis reactor may be separated, for example by distillation, to produce an overhead stream comprising the 1-decene and a bottoms stream comprising the 9-decanoic acid. In such an embodiment, the 1-decene may be routed to an existing kerosene/jet fuel hydrotreater for saturation to decane without the 9-decanoic acid affecting the hydrotreating catalyst. Thereafter the decane may be sent straight to a jet blending pool.

In another embodiment, jet range hydrocarbons may be produced from hydrotreating the fatty acids produced in the hydrolysis reactor to produce the corresponding saturated fatty acids. As discussed above, a product from the hydrolysis reactor may include C18s, such as stearic acid (C18:0), oleic acid (C18:1), and linoleic acid (C18:2), for example. The hydrotreatment of the C18s may convert at least a portion of the C18:1 and C18:2 fatty acids to produce saturated products including stearic acid. The stearic acid, and any unreacted C18:1 and C18:2, if present, may be introduced into a hydrocracking unit under conditions sufficient to hydrocrack at least a portion of the molecules to produce jet range hydrocarbons.

FIG. 1 is a block flow diagram illustrating a process producing jet range hydrocarbons from triglycerides in accordance with some embodiments disclosed herein. In FIG. 1, a triglyceride stream 2 may be introduced into hydrolysis unit 10. Triglyceride stream 2 may include any of the triglycerides discussed above. In hydrolysis unit 10, triglycerides from triglyceride stream 2 may be reacted with steam to produce the corresponding fatty acids from the triglycerides as well as glycerol. Hydrolysis unit 10 may include various different equipment for hydrolyzing the triglyceride with steam, including but not limited to, hydrolysis reactors such as hydrolysis reactors 104 on FIG. 2. For example, the hydrolysis unit may include a batch reactor or a continuous reactor such as a column reactor. In some examples the hydrolysis unit may be configured to perform the Colgate-Emery process and include the associated reactors, flash tanks, and settling tanks required.

At least a portion of the triglycerides produced may be C18:1 oleic acid. Intermediate stream 3 containing at least a portion of the fatty acids from hydrolysis unit 10 may be introduced into olefin cross-metathesis unit 112. In olefin cross-metathesis unit 112, the C18:1 may be reacted with ethylene in the presence of a Grubbs catalyst to produce 1-decene and 9-decanoic acid. Intermediate stream 4 containing at least a portion of the 1-decene and 9-decanoic acid produced in olefin cross-metathesis unit 112 may be introduced into hydrotreating unit 30. Hydrotreating unit 30 may include reactors comprising hydrotreating catalysts, heaters, separators, and columns configured to perform hydrotreating operations. Hydrotreating may include a range of catalytic processes which react an input stream with hydrogen over a catalyst bed to add hydrogen to the input stream. In hydrotreating unit 30, at least a portion of the 1-decene and 9-decanoic acid from intermediate stream 4 may be hydrotreated to produce decane. Decane stream 5 may be introduced into isomerization unit 40 where at least a portion of the decane may be isomerized to iso-decane. Isomerization unit 40 may include isomerization reactors comprising an isomerization catalyst, as well as associated dryers, separation columns, pumps, and other equipment necessary to isomerize an input stream. Product stream 6, containing the iso-decane may be withdrawn from isomerization unit 40.

Figure 2:
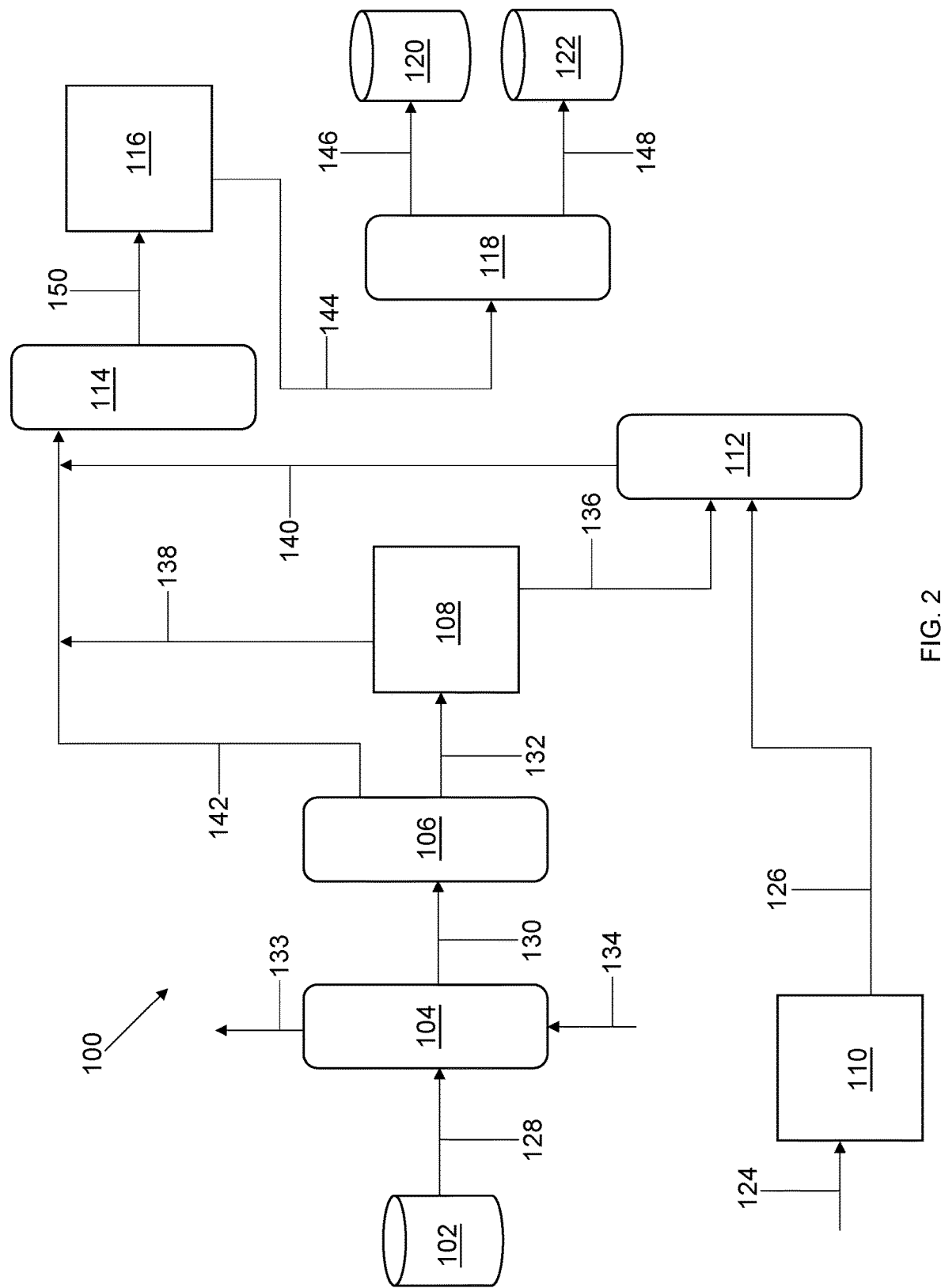
FIG. 2 is a schematic illustration of a process for producing jet range hydrocarbons from triglycerides.

FIG. 2 is a schematic illustration of a process 100 for producing jet range hydrocarbons from triglycerides in accordance with some embodiments disclosed herein. Process 100 may begin with triglyceride storage 102. Triglyceride storage 102 may be any storage system, such as a tank farm, barrels, pipeline, or any other suitable storage for the triglycerides described above. Triglycerides from triglyceride storage 102 may be conveyed to hydrolysis reactor 104 through conveyance 128. Conveyance 128 may include pipes, tubulars, pumps, and other equipment required to convey the triglycerides from triglyceride storage 102 to hydrolysis reactor 104.

Hydrolysis reactor 104 may be any of the previously mentioned reactor types such as batch reactor or column-type reactor. Steam stream 134 may be introduced into hydrolysis reactor 104 and be contacted with triglycerides provided from conveyance 128. The triglycerides may be hydrolyzed to form the corresponding fatty acids and glycerol as described above. Hydrolysis reactor 104 may be operated at any of the conditions described above. Glycerol as well as water and/or steam may be withdrawn from hydrolysis reactor 104 as stream 133 and the free fatty acid may be withdrawn from hydrolysis reactor 104 as stream 130. In some embodiments, additional glycerol removal may be utilized such as aqueous phase absorption of the glycerol, followed by phase separation from the fatty acids. Fatty acids in stream 130 may include a range of fatty acids, the carbon number of which depends on the carbon numbers of the triglycerides which were hydrolyzed. In some embodiments, stream 130 may include fatty acids with carbon number ranging from C6 to C22, for example.

Stream 130 containing the produced fatty acids may be introduced into distillation column 106 where the produced fatty acids may be fractionated by molecular weight into overhead stream 142 containing the fatty acids with carbon numbers of C17 and below and bottom stream 132 containing the fatty acids with carbon numbers of C18 and above, e.g., C18s. In separator 108, the C18s may be further separated into C18:1 stream 136 and fatty acid stream 138. C18:1 stream 136 may include a majority of the C18:1 fatty acid from bottom stream 132 while fatty acid stream 138 may contain a majority of the C18:0 and C18:2 from bottom stream 132. If additional fatty acids heavier than C18 are present in bottom stream 132, separator 108 may additionally separate the heavier fatty acids into fatty acid stream 138.

Ethanol stream 124 may be introduced to ethanol dehydrator 110 which may dehydrate the ethanol to produce ethylene stream 126. Ethanol dehydrator 110 may utilize any of the ethanol dehydration techniques disclosed herein to produce ethylene from ethanol. In some embodiments, ethanol dehydrator 110 may include a steam cracking furnace or other on-purpose units for producing ethylene. From ethanol dehydrator 110, ethylene stream 126 may be introduced into olefin cross metathesis unit 112.

From separator 108, C18:1 stream 136 may be introduced into olefin cross metathesis unit 112. Olefin cross metathesis unit 112 may include any of the previously described Grubbs catalysts including first, second, and/or third generation Grubbs catalyst. Olefin cross metathesis unit 112 may be operated at conditions suitable to react at least a portion of the ethylene from ethylene stream 126 and C18:1 fatty acid from stream 136 to produce 1-decene and 9-decanoic acid.

Product stream 140 containing the produced 1-decene and 9-decanoic acid may be withdrawn from olefin cross metathesis unit 112.

Overhead stream 142, fatty acid stream 138, and product stream 140 may be combined and introduced into hydrotreating unit 114. Hydrotreating unit 114 may include any hydrotreating units and catalysts previously described. Hydrotreating unit 114 may further include a hydrogen stream input such that the hydrotreating unit 114 may be operated at conditions suitable react at least a portion of the feed with the hydrogen to produce paraffins corresponding to olefins, saturated fatty acids, and unsaturated fatty acids in the feed to hydrotreating unit 114. Hydrotreated stream 150 may include decane as a reaction product corresponding to the 1-decene and 9-decanoic acid from product stream 140. Product stream 140 may further include paraffins corresponding to the fatty acids with carbon numbers of C17 from overhead stream 142 as well as paraffins corresponding to the fatty acids C18:0 and C18:2 from fatty acid stream 138.

Hydrotreated stream 150 may be introduced into isomerization unit 116. Isomerization unit 116 may include any of the previously described isomerization units and may be operated at conditions sufficient to isomerize at least a portion of the paraffins in hydrotreated stream 150 to the corresponding iso-paraffins including iso-decane corresponding to the 1-decene and 9-decanoic acid from product stream 140. For example, the isomerization unit may be operated at about 245 to about 270° C. and about 21 to about 35 kg/cm$^2$. Isomerized stream 144 may be withdrawn from isomerization unit 116 and introduced into product fractionator 118. Product fractionator 118 may include a distillation column, for example, configured to separate components of isomerized stream 144 into stream based on molecular mass. For example, product fractionator 118 may separate isomerized stream 144 into jet range hydrocarbon stream 146 comprising hydrocarbons from isomerized stream 144 with carbon numbers from 9 to 16 and diesel range hydrocarbon stream 148 comprising any other hydrocarbons from isomerized stream 144. Jet range hydrocarbon stream 146 may be send to jet mixing pool 120 while diesel range hydrocarbon stream 148 may be send to diesel mixing pool 122.

Figure 3:
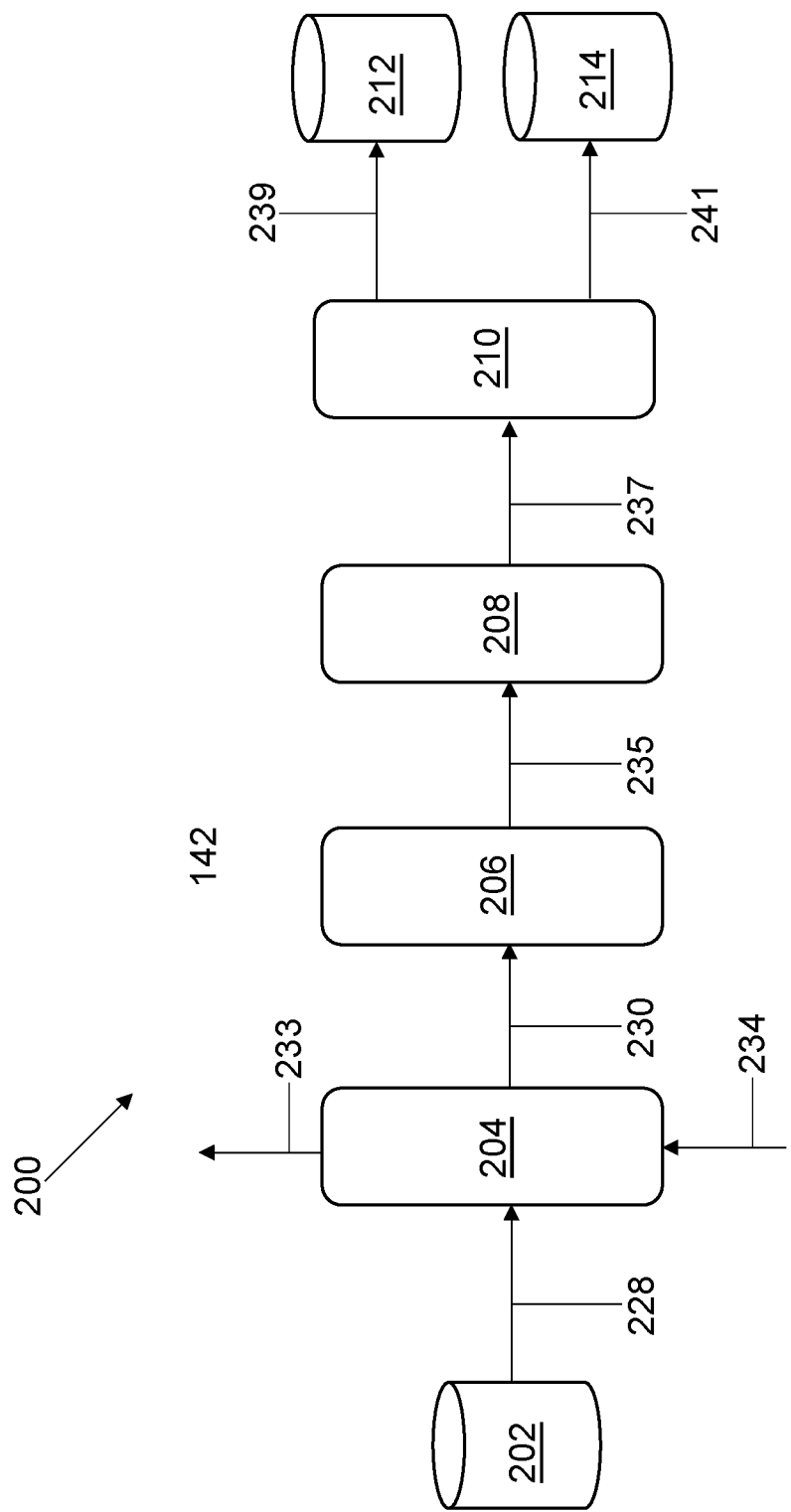
FIG. 3 is a schematic illustration of a process for producing jet range hydrocarbons from triglycerides.

FIG. 3 illustrates a process 300 for producing jet range hydrocarbons according to some embodiments disclosed herein. Process 200 may begin with triglyceride storage 202. Triglyceride storage 202 may be any storage system, such as a tank farm, barrels, pipeline, or any other suitable storage for the triglycerides described above. Triglycerides from triglyceride storage 202 may be conveyed to hydrolysis reactor 204 through conveyance 228. Conveyance 228 may include pipes, tubulars, pumps, and other equipment required to convey the triglycerides from triglyceride storage 202 to hydrolysis reactor 204.

Hydrolysis reactor 204 may be any of the previously mentioned reactor types such as batch reactor or column-type reactor. Steam stream 234 may be introduced into hydrolysis reactor 204 and be contacted with triglycerides provided from conveyance 228. The triglycerides may be hydrolyzed to form the corresponding fatty acids and glycerol as described above. Hydrolysis reactor 204 may be operated at any of the conditions described above. Glycerol as well as water and/or steam may be withdrawn from hydrolysis reactor 204 as stream 233 and the free fatty acid may be withdrawn from hydrolysis reactor 204 as stream 230. In some embodiments, additional glycerol removal may be utilized such as aqueous phase absorption of the glycerol, followed by phase separation from the fatty acids. Fatty acids in stream 230 may include a range of fatty acids, the carbon number of which depends on the carbon numbers of the triglycerides which were hydrolyzed. In some embodiments, stream 230 may include fatty acids with carbon number ranging from C6 to C22, for example.

Stream 230 may be introduced into hydrotreating unit 206. Hydrotreating unit 206 may include any hydrotreating units and catalysts previously described. Hydrotreating unit 206 may further include a hydrogen stream input such that the hydroprocessing unit may be operated at conditions suitable react at least a portion of the feed to hydrotreating unit 206 with the hydrogen to produce paraffins corresponding to saturated fatty acids and unsaturated fatty acids produced in hydrolysis reactor 204 and conveyed to hydrotreating unit 206 by stream 230. As discussed above, a product from the hydrolysis reactor may include C18s, such as stearic acid (C18:0), oleic acid (C18:1), and linoleic acid (C18:2), for example. The hydrotreatment of the C18s may convert at least a portion of the C18:1 and C18:2 fatty acids to produce saturated products including stearic acid. Hydrotreated stream 235 may be withdrawn from hydrotreating unit 206 and may be introduced into hydrocracker unit 208. In hydrocracker unit 208, a hydrogen stream and the paraffins produced in hydrotreating unit 206 may be reacted at conditions sufficient to crack paraffins present in hydrotreated stream 235 to shorter chain hydrocarbons such as saturated paraffins including jet range hydrocarbons. Hydrocracked stream 237 comprising the hydrocracked hydrocarbons from hydrocracker unit 208 Hydrocracked stream 237 from hydrocracker unit 208 may be introduced into product fractionator 210. Product fractionator 210 may include a distillation column, for example, configured to separate components of hydrocracked stream 237 into streams based on molecular mass. For example, product fractionator 210 may separate hydrocracked stream 237 into jet range hydrocarbon stream 239 comprising hydrocarbons from hydrocracked stream 237 with carbon numbers from 9 to 16 and diesel range hydrocarbon stream 241 comprising any other hydrocarbons from hydrocracked stream 237. Jet range hydrocarbon stream 239 may be send to jet mixing pool 212 while diesel range hydrocarbon stream 241 may be send to diesel mixing pool 214.

Accordingly, the preceding description describes methods and systems for producing jet range hydrocarbons from triglycerides sourced from natural sources including triglycerides. The processes and systems disclosed herein may include any of the various features disclosed herein, including one or more of the following embodiments.

Embodiment 1. A method for producing jet range hydrocarbons comprising: hydrolyzing a triglyceride stream in a hydrolysis unit to produce at least a C18:1 free fatty acid, wherein the triglyceride stream comprises at least one triglyceride comprising at least one C18:1 fatty acid, wherein hydrolyzing the triglyceride stream comprises contacting the at least one triglyceride from the triglyceride stream with at least one of water or steam at conditions sufficient to hydrolyze at least a portion of the at least one triglyceride to produce the C18:1 free fatty acid; introducing the C18:1 free fatty acid into an olefin cross-metathesis reactor and reacting at least a portion of the C18:1 free fatty acid with ethylene in the presence of a Grubbs catalyst to produce 1-decene and 9-decanoic acid; introducing the 1-decene and 9-decanoic acid into a hydrotreating unit and to hydrotreating at least a portion of the 1-decene and 9-decanoic acid to produce decane; and introducing the decane into an isomerization unit and isomerizing at least a portion of the decane to produce iso-decane.

Embodiment 2. The method of embodiment 1, wherein the triglyceride stream further comprises at least at least one additional unsaturated fatty acid molecule with a carbon chain length of at least C18 to C32 and at least one unsaturated bond on at least the 9th carbon or greater.

Embodiment 3. The method of any of embodiments 1-2, wherein the triglyceride stream further comprises at least one additional triglyceride comprising at least one fatty acid selected from the group consisting of C14 fatty acid, C15 fatty acid, C16 fatty acid, C18:0 fatty acid, C18:2 fatty acid, and combinations thereof, and wherein the method further comprises hydrolyzing the at least one additional triglyceride to produce at least one fatty acid selected from the group consisting of C14 fatty acid, C15 fatty acid, C16 fatty acid, C18:0 fatty acid, C18:2 fatty acid, and combinations thereof.

Embodiment 4. The method of embodiment 3, wherein an outlet from the hydrolysis unit comprises the C18:1 free fatty acid and the at least one additional triglyceride, and wherein the method further comprises fractionating the outlet from the hydrolysis unit to produce an overhead stream comprising C16 and lighter fatty acids and a bottoms stream comprising C18:2 and heavier fatty acids.

Embodiment 5. The method of embodiment 4, further comprising separating C18:1 free fatty acid from the bottoms stream, wherein the C18:1 free fatty acid separated from the bottoms stream is introduced in the olefin cross-metathesis reactor.

Embodiment 6. The method of any of embodiments 4-5, further comprising introducing the overhead stream comprising C16 and lighter fatty acids into the hydrotreating unit and hydrotreating at least a portion of the C16 and lighter fatty acids to produce a saturated paraffin corresponding to the C16 and lighter fatty acids.

Embodiment 7. The method of embodiment 6 wherein the saturated paraffin is introduced into the isomerization unit to isomerize at least a portion of the saturated paraffin to produce a corresponding iso-paraffin.

Embodiment 8. The method of any of embodiments 1-7, further comprising dehydrating an ethanol stream to produce an ethylene stream and introducing the ethylene stream into the olefin cross-metathesis reactor.

Embodiment 9. The method of any of embodiments 1-8, wherein the triglyceride stream is from an algae source.

Embodiment 10. A method for producing jet range hydrocarbons comprising: counter-currently contacting a triglyceride stream and steam in a column hydrolysis unit to produce at least a C18:1 free fatty acid stream, wherein the triglyceride stream comprises at least one triglyceride comprising at least one C18:1 fatty acid; introducing the C18:1 free fatty acid stream into an olefin cross-metathesis reactor and reacting at least a portion of the C18:1 free fatty acid with ethylene in the presence of a Grubbs catalyst to produce a 1-decene and 9-decanoic acid stream; introducing the 1-decene and 9-decanoic acid stream into a hydrotreating unit and hydrotreating at least a portion of the 1-decene and 9-decanoic acid to produce a decane stream; introducing the decane stream into an isomerization unit and isomerizing at least a portion of the decane stream to produce an iso-decane stream; and separating at least a portion of the iso-decane stream to produce a jet range hydrocarbon stream.

Embodiment 11. The method of embodiment 10, wherein the column hydrolysis unit is operated at about 245° C. to about 270° C. and about 21 to about 35 kg/cm$^2$.

Embodiment 12. The method of any of embodiments 10-11, wherein the column hydrolysis unit is operated at a temperature in a range of about 250° C. to about 260° C. and a pressure up to 50 barg, and wherein 95% or greater of the triglyceride stream by weight is converted to a corresponding fatty acid.

Embodiment 13. A system for producing jet range hydrocarbons comprising: a triglyceride source comprising at least one C18:1 fatty acid; a hydrolysis unit coupled to the triglyceride source and a steam source, wherein the hydrolysis unit is configured to hydrolyze at least a portion of the triglyceride source to produce a free fatty acid stream comprising free fatty acids corresponding to triglycerides in the triglyceride source, wherein the free fatty acid stream comprises at least C18:1 fatty acid; a separation unit coupled to the free fatty acid stream, wherein the separation unit is configured to separate a majority of the C18:1 fatty acid from the free fatty acid stream to produce a C18:1 fatty acid stream; an olefin cross metathesis reactor coupled to the C18:1 fatty acid stream, wherein the olefin cross metathesis reactor is configured to react the C18:1 fatty acid with ethylene to produce a stream comprising 1-decene and 9-decanoic acid; a hydrotreating unit coupled to the stream comprising 1-decene and 9-decanoic acid, wherein the hydrotreating unit is configured to hydrotreat at least a portion of the 1-decene and 9-decanoic acid to produce a hydrotreated product stream comprising decane; and an isomerization unit coupled to the hydrotreated product stream, wherein the isomerization unit is configured to isomerize at least a portion of the decane to produce an isomerized product stream comprising iso-decane.

Embodiment 14. The system of embodiment 13, wherein the triglyceride source further comprises at least one additional triglyceride comprising at least one fatty acid selected from the group consisting of C14 fatty acid, C15 fatty acid, C16 fatty acid, C18:0 fatty acid, C18:2 fatty acid, and combinations thereof.

Embodiment 15. The system of any of embodiments 13-14 wherein the steam source comprises steam at a temperature in a range of about 250° C.-260° C. and a pressure up to 50 barg.

Embodiment 16. The system of any of embodiments 13-15 wherein the olefin cross metathesis reactor further comprises a Grubbs catalyst.

Embodiment 17. The system of any of embodiments 13-16 wherein the separation unit is further configured to produce a stream containing a balance of the fatty acids from the free fatty acid stream which are not the C18:1 fatty acid.

Embodiment 18. The system of embodiment 17 wherein the stream containing the balance of the fatty acids is coupled to the hydrotreating unit and where the hydrotreating unit is further configured to hydrotreat at least a portion of the balance of the fatty acids to produce paraffins, wherein the hydrotreated product stream comprises the paraffins.

Embodiment 19. The system of embodiment 18 wherein the isomerization unit is further configured to isomerize the paraffins to iso-paraffins, wherein the isomerized product stream further comprises the iso-paraffins.

Embodiment 20. The system of any of embodiments 18-19, further comprising a product fractionator configured to separate the isomerized stream into a jet range hydrocarbon stream and diesel range hydrocarbon stream.

While the disclosure has been described with respect to a number of embodiments and examples, those skilled in the art, having benefit of this disclosure, will appreciate that other embodiments can be devised which do not depart from the scope and spirit of the disclosure as disclosed herein. Although individual embodiments are discussed, the present disclosure covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the disclosure, additionally, they do not exclude impurities and variances normally associated with the elements and materials used.

All numerical values within the detailed description and the claims herein modified by "about" or "approximately" with respect the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

What is claimed is:

1. A method for producing jet range hydrocarbons comprising:
   providing a triglyceride stream comprising at least one C18:1 fatty acid;
   hydrolyzing the triglyceride stream in a hydrolysis unit to produce at least one C18:1 free fatty acid, wherein the hydrolyzing comprises contacting the at least one C18:1 fatty acid with steam at conditions sufficient to hydrolyze at least a portion of the at least one C18:1 fatty acid to produce the C18:1 free fatty acid;
   introducing the C18:1 free fatty acid into an olefin cross-metathesis reactor and reacting at least a portion of the C18:1 free fatty acid with ethylene in the presence of a Grubbs catalyst to produce 1-decene and 9-decenoic acid;
   introducing the 1-decene and 9-decenoic acid into a hydrotreating unit and hydrotreating at least a portion of the 1-decene and 9-decenoic acid to produce decane; and
   introducing the decane into an isomerization unit and isomerizing at least a portion of the decane to produce iso-decane.

2. The method of claim 1, wherein the triglyceride stream further comprises at least one additional unsaturated fatty acid molecule with a carbon chain length of at least C18 to C32 and at least one unsaturated bond on at least the 9th carbon or greater.

3. The method of claim 1, wherein the triglyceride stream further comprises at least one additional triglyceride comprising at least one fatty acid selected from the group consisting of C14 fatty acid, C15 fatty acid, C16 fatty acid, C18:0 fatty acid, C18:2 fatty acid, and combinations thereof, and wherein the method further comprises hydrolyzing the at least one additional triglyceride to produce at least one fatty acid selected from the group consisting of C14 fatty acid, C15 fatty acid, C16 fatty acid, C18:0 fatty acid, C18:2 fatty acid, and combinations thereof.

4. The method of claim 3, wherein an outlet from the hydrolysis unit comprises the C18:1 free fatty acid and the at least one additional triglyceride, and wherein the method further comprises fractionating the outlet from the hydrolysis unit to produce an overhead stream comprising C16 and lighter fatty acids and a bottoms stream comprising C18:2 and heavier fatty acids.

5. The method of claim 4, further comprising separating C18:1 free fatty acid from the bottoms stream, wherein the C18:1 free fatty acid separated from the bottoms stream is introduced in the olefin cross-metathesis reactor.

6. The method of claim 4, further comprising introducing the overhead stream comprising C16 and lighter fatty acids into the hydrotreating unit and hydrotreating at least a portion of the C16 and lighter fatty acids to produce a saturated paraffin corresponding to the C16 and lighter fatty acids.

7. The method of claim 6 wherein the saturated paraffin is introduced into the isomerization unit to isomerize at least a portion of the saturated paraffin to produce a corresponding iso-paraffin.

8. The method of claim 1, further comprising dehydrating an ethanol stream to produce an ethylene stream and introducing the ethylene stream into the olefin cross-metathesis reactor.

9. The method of claim 1, wherein the triglyceride stream is from an algae source.

10. A method for producing jet range hydrocarbons comprising:
    counter-currently contacting a triglyceride stream and steam in a column hydrolysis unit to produce at least a C18:1 free fatty acid stream, wherein the triglyceride stream comprises at least one triglyceride comprising at least one C18:1 fatty acid;
    introducing the C18:1 free fatty acid stream into an olefin cross-metathesis reactor and reacting at least a portion of the C18:1 free fatty acid with ethylene in the presence of a Grubbs catalyst to produce a 1-decene and 9-decenoic acid stream;
    introducing the 1-decene and 9-decenoic acid stream into a hydrotreating unit and hydrotreating at least a portion of the 1-decene and 9-decenoic acid to produce a decane stream;
    introducing the decane stream into an isomerization unit and isomerizing at least a portion of the decane stream to produce an iso-decane stream; and
    separating at least a portion of the iso-decane stream to produce a jet range hydrocarbon stream.

11. The method of claim 10, wherein the column hydrolysis unit is operated at about 245° C. to about 270° C. and about 21 to about 35 kg/cm$^2$.

12. The method of claim 10, wherein the column hydrolysis unit is operated at a temperature in a range of about 250° C. to about 260° C. and a pressure up to 50 barg, and wherein 95% or greater of the triglyceride stream by weight is converted to a corresponding fatty acid.

13. A system for producing jet range hydrocarbons comprising:
    a triglyceride source comprising at least one C18:1 fatty acid;
    a hydrolysis unit coupled to the triglyceride source and a steam source, wherein the hydrolysis unit is configured to hydrolyze at least a portion of the triglyceride source to produce a free fatty acid stream comprising free fatty acids corresponding to triglycerides in the triglyceride source, wherein the free fatty acid stream comprises at least C18:1 fatty acid;
    a separation unit coupled to the free fatty acid stream, wherein the separation unit is configured to separate a majority of the C18:1 fatty acid from the free fatty acid stream to produce a C18:1 fatty acid stream;

an olefin cross metathesis reactor coupled to the C18:1 fatty acid stream, wherein the olefin cross metathesis reactor is configured to react the C18:1 fatty acid with ethylene to produce a stream comprising 1-decene and 9-decenoic acid;

a hydrotreating unit coupled to the stream comprising 1-decene and 9-decanoic acid, wherein the hydrotreating unit is configured to hydrotreat at least a portion of the 1-decene and 9-decenoic acid to produce a hydrotreated product stream comprising decane; and an isomerization unit coupled to the hydrotreated product stream, wherein the isomerization unit is configured to isomerize at least a portion of the decane to produce an isomerized product stream comprising iso-decane.

14. The system of claim 13, wherein the triglyceride source further comprises at least one additional triglyceride comprising at least one fatty acid selected from the group consisting of C14 fatty acid, C15 fatty acid, C16 fatty acid, C18:0 fatty acid, C18:2 fatty acid, and combinations thereof.

15. The system of claim 13 wherein the steam source comprises steam at a temperature in a range of about 250° C.-260° C. and a pressure up to 50 barg.

16. The system of claim 13 wherein the olefin cross metathesis reactor further comprises a Grubbs catalyst.

17. The system of claim 13 wherein the separation unit is further configured to produce a stream containing a balance of the fatty acids from the free fatty acid stream which are not the C18:1 fatty acid.

18. The system of claim 17 wherein the stream containing the balance of the fatty acids is coupled to the hydrotreating unit and where the hydrotreating unit is further configured to hydrotreat at least a portion of the balance of the fatty acids to produce paraffins, wherein the hydrotreated product stream comprises the paraffins.

19. The system of claim 18 wherein the isomerization unit is further configured to isomerize the paraffins to iso-paraffins, wherein the isomerized product stream further comprises the iso-paraffins.

20. The system of claim 18, further comprising a product fractionator configured to separate the isomerized stream into a jet range hydrocarbon stream and diesel range hydrocarbon stream.

* * * * *